(12) United States Patent
Oki et al.

(10) Patent No.: US 10,805,511 B2
(45) Date of Patent: Oct. 13, 2020

(54) CONTROLLING A SET OF LIGHT SOURCES BY INDIVIDUAL ADJUSTMENT TO OUTPUT A DESIRED LIGHT

(71) Applicant: SONY CORPORATION, Tokyo (JP)

(72) Inventors: Tomoyuki Oki, Kanagawa (JP); Akio Furukawa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/306,130

(22) PCT Filed: Mar. 13, 2015

(86) PCT No.: PCT/JP2015/057488
§ 371 (c)(1),
(2) Date: Oct. 24, 2016

(87) PCT Pub. No.: WO2015/166728
PCT Pub. Date: Nov. 5, 2015

(65) Prior Publication Data
US 2017/0048435 A1 Feb. 16, 2017

(30) Foreign Application Priority Data
May 1, 2014 (JP) ................................ 2014-094653

(51) Int. Cl.
*H04N 5/225* (2006.01)
*A61B 1/06* (2006.01)
(Continued)

(52) U.S. Cl.
CPC ....... *H04N 5/2256* (2013.01); *A61B 1/00006* (2013.01); *A61B 1/0638* (2013.01);
(Continued)

(58) Field of Classification Search
CPC .................................. H04N 9/44; H04N 9/73
See application file for complete search history.

(56) References Cited

U.S. PATENT DOCUMENTS 8,535,221 B2 * 9/2013 Saito .................. A61B 1/00009
600/109
8,803,056 B2 * 8/2014 Shirota .................. G02B 23/26
250/205

(Continued)

FOREIGN PATENT DOCUMENTS

JP 2009-034224 A 2/2009
JP 2012-029728 A 2/2012

(Continued)

OTHER PUBLICATIONS

Office Action dated Apr. 14, 2020 in Japanese Patent Application No. 2019-120440, 14 pages.

*Primary Examiner* — Francis Geroleo
*Assistant Examiner* — Christopher Kingsbury Glover
(74) *Attorney, Agent, or Firm* — Xsensus LLP

(57) ABSTRACT

An illuminating device includes an image acquisition system configured to adjust a plurality of light sources on the basis of a correlation between luminance acquired from an image processing device and the light amounts of the emission light beams. Accordingly, the color temperature of the image processing device can be accurately adjusted because the illuminating device can control the plurality of light sources by individual adjustment to output a desired light.

14 Claims, 12 Drawing Sheets

(51) Int. Cl.
*A61B 1/00* (2006.01)
*H05B 45/20* (2020.01)
*H05B 47/20* (2020.01)
*H05B 47/105* (2020.01)
*H04N 9/73* (2006.01)

(52) U.S. Cl.
CPC ........... *A61B 1/0669* (2013.01); *H04N 9/735* (2013.01); *H05B 45/20* (2020.01); *H05B 47/105* (2020.01); *H05B 47/20* (2020.01); *H04N 2005/2255* (2013.01)

(56) References Cited

U.S. PATENT DOCUMENTS

| | | | |
|---|---|---|---|
| 2009/0121641 A1* | 5/2009 | Shih | G01J 1/1626 315/157 |
| 2010/0225241 A1* | 9/2010 | Maehara | H05B 33/086 315/250 |
| 2016/0374602 A1* | 12/2016 | Koshiba | H04N 5/3456 600/327 |

FOREIGN PATENT DOCUMENTS

| | | |
|---|---|---|
| JP | 2012-066066 A | 4/2012 |
| JP | 2014-000301 A | 1/2014 |
| WO | WO 2006134029 A1 * 12/2006 | ........... G09G 3/3413 |
| WO | 2010/070720 A | 6/2010 |
| WO | 2010/070720 A1 | 6/2010 |
| WO | 2013/150897 A1 | 10/2013 |
| WO | 2014/034184 A | 3/2014 |
| WO | 2014/034184 A1 | 3/2014 |

* cited by examiner

CONTROLLING A SET OF LIGHT SOURCES BY INDIVIDUAL ADJUSTMENT TO OUTPUT A DESIRED LIGHT

CROSS REFERENCE TO RELATED APPLICATIONS

This application is a U.S. National Phase of International Patent Application No. PCT/JP2015/057488 filed on Mar. 13, 2015, which claims priority benefit of Japanese Patent Application No. JP 2014-094653 filed in the Japan Patent Office on May 1, 2014. Each of the above-referenced applications is hereby incorporated herein by reference in its entirety.

TECHNICAL FIELD

The present disclosure relates to an illuminating device, a control method for an illuminating device, and an image acquisition system.

BACKGROUND ART

There have been conventionally proposed techniques of using light sources for R, G, and B in image acquisition systems such as endoscopes and microscopic cameras instead of lamp light sources such as xenon lamps and halogen lamps. For example, Patent Literature 1: JP 2012-29728A discloses a light source device including a visible light LED having independent light sources for R, G, and B as an imaging system applicable to endoscopes and microscopic cameras.

In Patent Literature 1: JP 2012-29728A, the intensity of emission light beams having respective colors of R, G, and B is adjusted with the visible light LED for all R, G, and B turned on, thereby adjusting the white balance of outputs from an image sensor. Specifically, Patent Literature 1: JP 2012-29728A describes that the intensity of emission light beams having respective colors of R, G, and B is adjusted on the basis of a color temperature detected by a white balance adjustment device on the basis of the outputs from the image sensor in order to adjust the white balance. In addition, Patent Literature 1: JP 2012-29728A describes that the intensity of emission light beams having respective colors of R, G, and B is adjusted according to an input by a user looking at monitor display based on the outputs from the image sensor in order to adjust the white balance.

CITATION LIST

Patent Literature

Patent Literature 1: JP 2012-29728A

SUMMARY OF INVENTION

Technical Problem

The white balance adjustment method described in Patent Literature 1: JP 2012-29728A, however, carries out white balance adjustment on the basis of the outputs from the image sensor on the color temperature of the illumination light obtained by multiplexing emission light beams from the independent light sources for R, G, and B with reference to monitor display. It is thus necessary to adjust the intensity of emission light beams having respective colors of R, G, and B while acquiring outputs from the image sensor every time the illumination light at a desired color temperature is emitted.

Accordingly, the present disclosure proposes a novel and improved illuminating device, control method for an illuminating device, and image acquisition system that can adjust each of the light amounts of a plurality of light sources on the basis of the correlation between luminance acquired from a light receiving unit and the light amounts of the emission light beams, and accurately adjust the color temperature of the light receiving unit.

Solution to Problem

According to the present disclosure, there is provided an illuminating device including: a plurality of light sources capable of adjusting light amounts of emission light beams; a light monitor unit configured to detect each of light amounts of emission light beams; and a control unit configured to control the light amounts of the emission light beams on the basis of a correlation between luminance acquired from a light receiving unit and the light amounts of the emission light beams.

Furthermore, according to the present disclosure, there is provided a control method for an illuminating device, the control method including: a step of detecting each of light amounts of emission light beams emitted from a plurality of light sources; and a step of controlling the light amounts of the emission light beams from the plurality of light sources on the basis of a correlation between luminance acquired from a light receiving unit and the light amounts of the emission light beams.

Still furthermore, according to the present disclosure, there is provided an image acquisition system including: a plurality of light sources capable of adjusting light amounts of emission light beams; a light monitor unit configured to detect each of light amounts of emission light beams; a light receiving unit configured to receive the emission light beams; and a control unit configured to control each of the light amounts of the emission light beams on the basis of a correlation between luminance detected by the light receiving unit and the light amounts of the emission light beams.

Advantageous Effects of Invention

According to the present disclosure as described above, it is possible to adjust each of the light amounts of a plurality of light sources on the basis of the correlation between luminance acquired from a light receiving unit and the light amounts of the emission light beams, and to accurately adjust the color temperature of the light receiving unit. Note that the effects described above are not necessarily limitative. With or in the place of the above effects, there may be achieved any one of the effects described in this specification or other effects that may be grasped from this specification.

DESCRIPTION OF EMBODIMENT(S)

Figure 1:
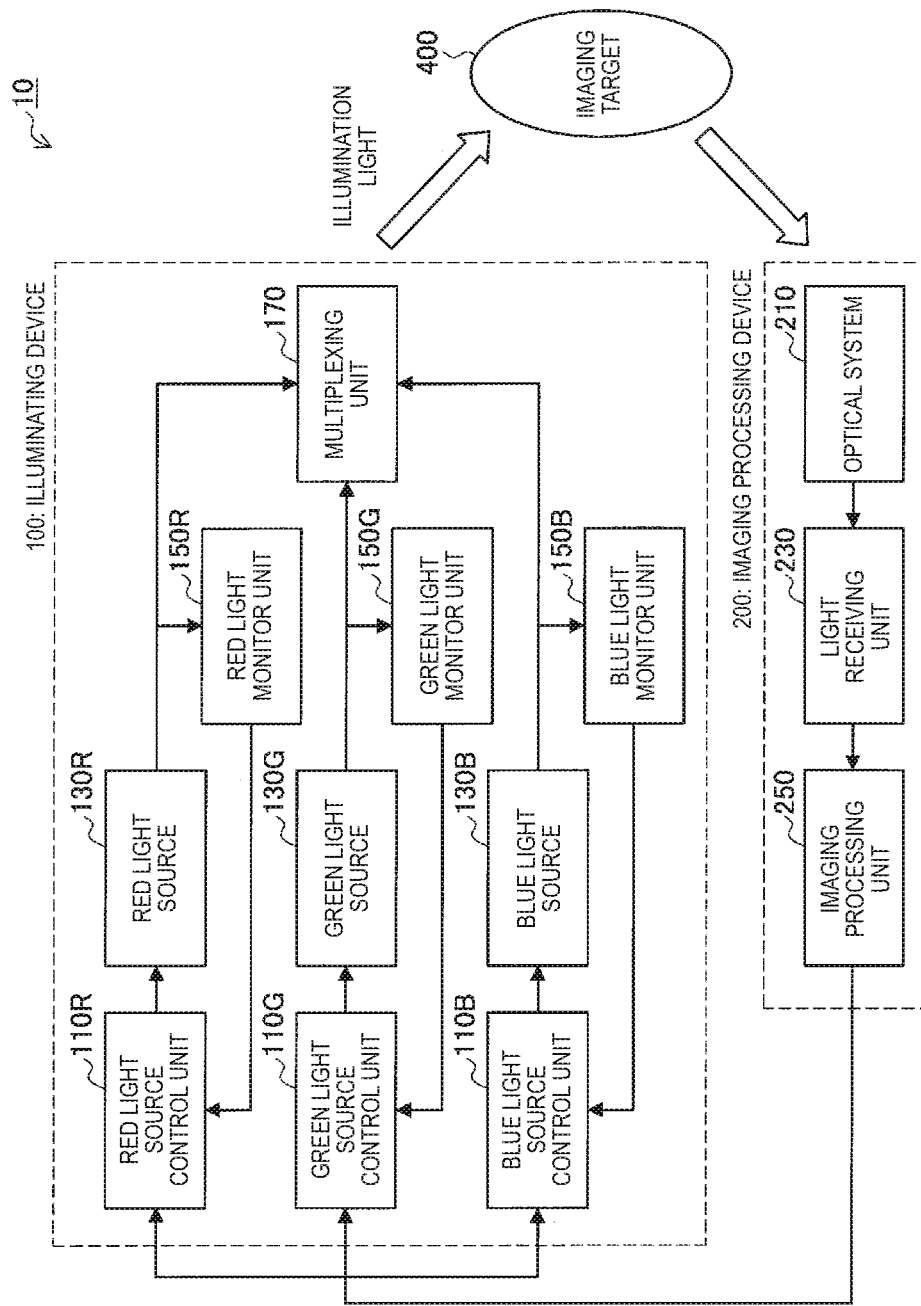
FIG. 1 is a block diagram illustrating an image acquisition system according to a first embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

A description will be now made in the following order.
<1. First embodiment (example in which control unit is provided to each light source)>
[1.1. Overall configuration example of image acquisition system]
(1.1.1. Configuration example of illuminating device)
(1.1.2. Configuration example of imaging processing device)
[1.2. Control processing example of illuminating device]
(1.2.1. White balance adjustment processing example)
(1.2.2. Color temperature adjustment processing example)
(1.2.3. Light amount adjustment processing example)
<2. Second embodiment (example in which common control unit is provided to all light sources)>
<3. Third embodiment (example in which deterioration determination processing function of light source is provided)>

"Emission light beams" herein refer to light emitted from a light source, and "illumination light" refers to light radiated from an illuminating device.

1. First Embodiment 1.1. Overall Configuration Example of Image Acquisition System First of all, the schematic configuration of an image acquisition system 10 according to a first embodiment of the present disclosure will be described with reference to FIG. 1. FIG. 1 is a block diagram illustrating the overall configuration of the image acquisition system 10 according to the present embodiment. This image acquisition system 10 includes an illuminating device 100 and an imaging processing device 200, and is configured, for example, as an endoscopic system. However, the endoscopic system is an example of the image acquisition system 10, so that the image acquisition system 10 may be another system such as an electronic microscope device.

1.1.1. Configuration Example of Illuminating Device

The illuminating device 100 includes a red light source 130R, a green light source 130G, a blue light source 130B, a red light source control unit 110R, a green light source control unit 110G, a blue light source control unit 110B, and a multiplexing unit 170. The illuminating device 100 further includes a red light monitor unit 150R, a green light monitor unit 150G, and a blue light monitor unit 150B.

The red light source 130R includes a semiconductor laser such as a GaInP quantum well structure laser diode, and a blue light source 130B includes a semiconductor laser such as a GaInN quantum well structure laser diode. The green light source 130G includes a solid-state laser that is excited, for example, by a semiconductor laser. The light source of the illuminating device 100 according to the present embodiment includes light sources for three colors R, G, and B implemented by controlling semiconductor lasers. Accordingly, different from lamp light sources such as xenon lamps and halogen lamps, the illuminating device 100 can electrically adjust the light amount of illumination light and the color temperature of the illumination light.

Figure 2:
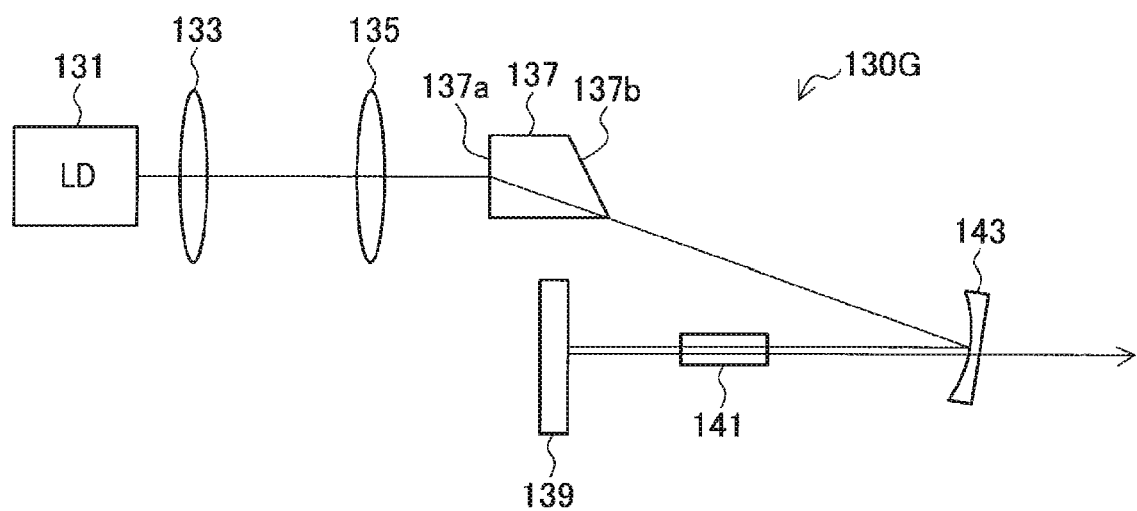
FIG. 2 is a schematic diagram illustrating an example of a configuration of a green light source according to the embodiment.

FIG. 2 is a schematic diagram illustrating a configuration example of the green light source 130G including a solid-state laser. The green light source 130G exemplified in FIG. 2 includes an excitation light source 131 including an AlGaAs quantum well structure laser diode, a condensing lenses 133 and 135, and an optical crystal 137 including YVO4. Further, the green light source 130G includes a resonator mirror 139, a wavelength conversion element 141 made of PPMgSLT, and a reflection unit 143 made of a concave mirror. The condensing lenses 133 and 135 and the optical crystal 137 are disposed in this order on the light path of light emitted from the excitation light source 131.

One end face of the optical crystal 137 on the side of the excitation light source 131 is configured to be a vertical face perpendicular to the optical axis and configured to be a resonator mirror having a high reflection film 137a. Further, the other end face of the optical crystal 137 is configured to be a slanted face having an angle except the Brewster's angle, and this slanted face is provided with an anti-reflection film 137b. The reflection unit 143 is disposed on the emission light path of light emitted from the optical crystal 137. The wavelength conversion element 141 is disposed on the light path of the light reflected by the reflection unit 143. The wavelength conversion element 141 is provided with anti-reflection films on both faces thereof. The resonator mirror 139 is provided on the opposite side of the wavelength conversion element 141 from the reflection unit 143.

In this green light source 130G, the excitation light emitted from the excitation light source 131 is configured to be a basic wave having a beam shape through the condensing lenses 133 and 135 to enter the optical crystal 137. The optical crystal 137 is excited by the incident light to emit new laser light. The emitted light is reflected by the reflection unit 143 to be radiated to the wavelength conversion element 141, transmitted through the wavelength conversion element 141, and reflected by the resonator mirror 139. The light emitted from the wavelength conversion element 141 is a conversion wave and the conversion wave is emitted as emission light beams after having transmitted through the reflection unit 143.

Note that the above described semiconductor laser and solid-state laser are examples of the red light source 130R, green light source 130G, and the blue light source 130B, and another light source may be used. The green light source 130G may be configured with a semiconductor laser. Further, the plurality of light sources are not limited to the light sources for three colors R, G, and B, and the number of light sources is not limited as in light sources for four colors or the like. Here, if a laser light source is used, diffusion of emission light beams is suppressed and the light amount can be detected easily by a light monitor unit.

The red light monitor unit 150R, the green light monitor unit 150G, and the blue light monitor unit 150B are configured with photodiodes, for example. The red light monitor unit 150R detects the light amount Qr of the emission light beams from the red light source 130R. The green light monitor unit 150G detects the light amount Qg of the emission light beams from the green light source 130G. The blue light monitor unit 150B detects the light amount Qb of the emission light beams from the blue light source 130B. Explaining the red light monitor unit 150R, the red light monitor unit 150R configured with the photodiode receives a part of the emission light beams (red light) emitted from the red light source 130R, converts the light amount Qr of the received light into a voltage signal, and transmits the voltage signal to the red light source control unit 110R. Similarly, the green light monitor unit 150G and the blue light monitor unit 150B receive parts of green light and blue light, convert the light amounts Qg and Qb of the received light beams into voltage signals, and transmit the voltage signals to the green light source control unit 110G and the blue light source control unit 110B, respectively.

The multiplexing unit 170 multiplexes the red light, the green light, and the blue light respectively emitted from the red light source 130R, the green light source 130G, and the blue light source 130B. In the illuminating device 100 according to the present embodiment, by the adjustment of the light amounts Qr, Qg, and Qb of the respective red light, green light, and blue light, the balance among luminance values Lr, Lg, and Lb of the respective red light, green light, and blue light can be changed and the color temperature of the multiplexed light can be adjusted.

Figure 3:
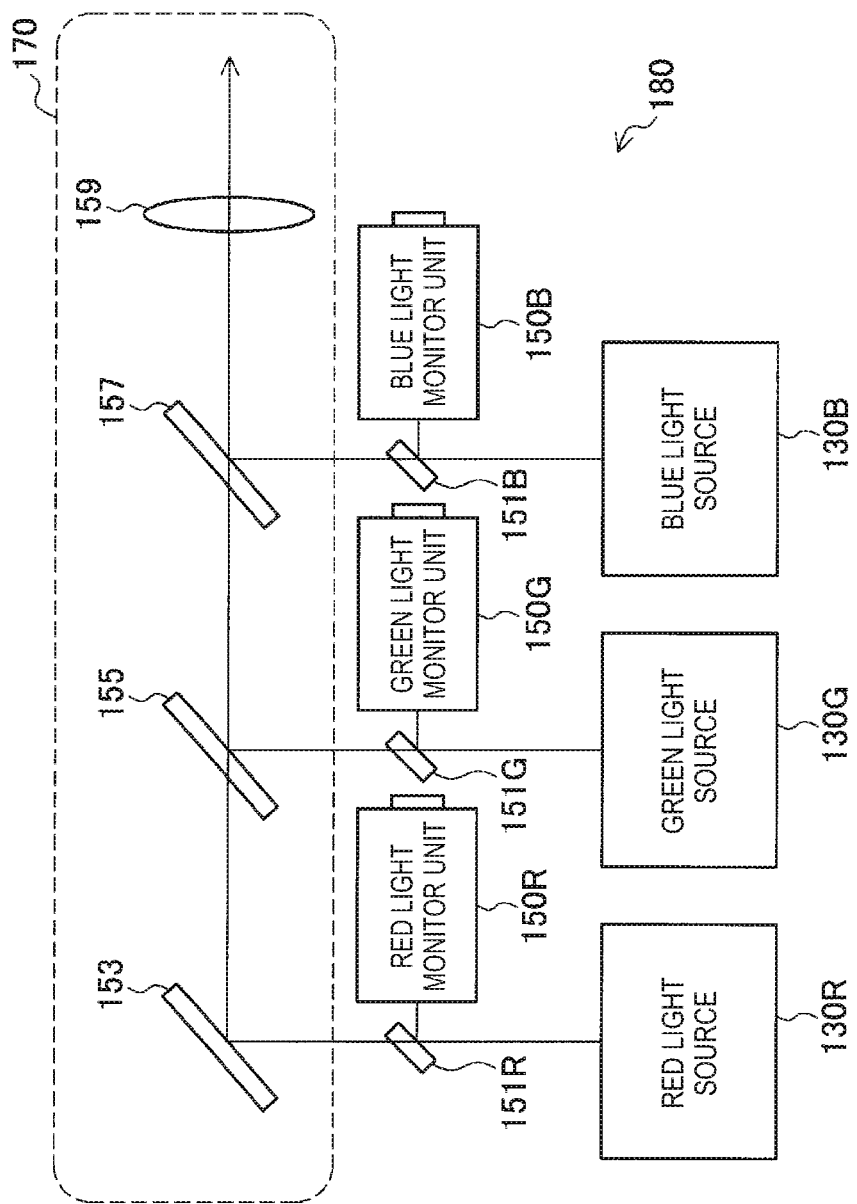
FIG. 3 is a schematic diagram illustrating an RGB multiplexing module including a light monitor unit according to the embodiment.

FIG. 3 is a schematic diagram illustrating a configuration example of the multiplexing unit 170, and illustrates a configuration example of a light-monitor-attached RGB multiplexing module 180. In this multiplexing module 180, the multiplexing unit 170 includes a mirror 153 and dichroic mirrors 155 and 157. The dichroic mirrors 155 and 157 reflect respective light beams having specific wavelengths. On the other side, each of the dichroic mirrors 155 and 157 transmits light having a wavelength except the specific wavelengths. The red light emitted from the red light source 130R is reflected by the mirror 153 and the travelling path thereof is changed to the direction toward a lens 159. The mirror 153 may be a dichroic mirror. Further, the green light emitted from the green light source 130G is reflected by the dichroic mirror 155 and the travelling path thereof is changed to the direction toward the lens 159. At this time, the red light transmitted from the mirror 153 is transmitted through the dichroic mirror 155 without change.

Furthermore, the blue light emitted from the blue light source 130B is reflected by the dichroic mirror 157 and the travelling path thereof is changed to the direction toward the lens 159. At this time, the red light and the green light transmitted from the dichroic mirror 155 are transmitted through the dichroic mirror 157 without change. In this manner, the light beams having the three colors R, G, and B are guided onto the same optical axis to be overlapped with each other. In this example of the multiplexing module 180, to the red light having the longest wavelength, the green light having the next longest wavelength is multiplexed and further the blue light having the shortest wavelength is multiplexed. The multiplexed light is further condensed by the lens 159 to be emitted as illumination light. In the case of an endoscopic system according to the present embodiment, the emitted illumination light is transmitted to the tip of an endoscope probe and radiated to illuminate a target portion.

Further, in the multiplexing module 180, a part of the red light emitted from the red light source 130R is input into the red light monitor unit 150R by the use of a light sampler 151R before the multiplexing. Thereby, the light amount Qr of the red light can be detected. Similarly, the parts of the green light and the blue light emitted from the green light source 130G and the blue light source 130B are input into the green light monitor unit 150G and the blue light monitor unit 150B by the use of light samplers 151G and 151B, respectively, and the light amounts Qg and Qb can be detected.

The red light source control unit 110R illustrated in FIG. 1 drives and controls the red light source 130R. Further, the green light source control unit 110G drives and controls the green light source 130G, and the blue light source control unit 110B drives and controls the blue light source 130B. Each of the control units controls the drive current in each of the light sources on the basis of a correlation between the luminance Lr (Lg or Lb) detected by a light receiving unit 230 in the imaging processing device 200 and the light amount Qr (Qg or Qb) detected by each of the light monitor units. For example, the red light source control unit 110R controls the drive current to be supplied to the red light source 130R on the basis of the correlation between the luminance Lr detected by the light receiving unit 230 and the light amount Qr of the red light detected by the red light monitor unit 150R.

Thereby, the light amount of the emission light beams emitted from the red light source 130R is adjusted, and the luminance Lr of the red light in the illumination light can be adjusted to a desirable value. The red light source control unit 110R according to the present embodiment is configured so as to calculate the correlation between the luminance Lr detected by the light receiving unit 230 and the light amount Qr of the red light detected by the red light monitor unit 150R when only the red light source 130R is turned on. At this time, the green light source 130G and the blue light source 130B are not turned on.

Similarly, the green light source control unit 110G and the blue light source control unit 110B are configured so as to calculate the correlations between the light amounts Qg and Qb detected by the green light monitor unit 150G and the blue light monitor unit 150B and the luminance values Lg and Lb detected by the light receiving unit 230, respectively. That is, the green light source control unit 110G and the blue light source control unit 110B calculate the correlations between the light amounts Qg and Qb and the luminance values Lg and Lb when only the green light source 130G or the blue light source 130B is turned on, respectively. The green light source control unit 110G and the blue light source control unit 110B control drive current to be supplied to the green light source 130G and the blue light source 130B on the basis of the correlations between the luminance values Lg and Lb and the light amounts Qg and Qb, respectively. Thereby, the light amounts Qg and Qb of the emission light beams emitted from the green light source 130G and the blue light source 130B can be adjusted, and the luminance values Lg and Lb of the green light and the blue light in the illumination light can be adjusted to desirable values, respectively.

In the illuminating device 100 according to the present embodiment, the drive currents of the respective light sources are adjusted on the basis of the correlations between the luminance values Lr, Lg, and Lb detected by the light receiving unit 230 of the imaging processing device 200 and the light amounts Qr, Qg, and Qb of the red light, the green light and the blue light detected by each of the light monitor units, respectively. Accordingly, in the case of the endoscopic system according to the present embodiment, for example, the correlations between the luminance values Lr, Lg, and Lb and the light amounts Qr, Qg, and Qb for the red light, the green light, and the blue light are acquired, respectively, during white balance adjustment which is performed always after the attachment of the endoscope probe. Thereby, after that, without reference to the luminance and the color temperature detected by the imaging processing device 200, the color temperature and the light amount of the illumination light can be adjusted accurately.

(1.1.2. Configuration Example of Imaging Processing Device)

The imaging processing device 200 includes an optical system 210, the light receiving unit 230, and an imaging processing unit 250. The optical system 210 takes in the illumination light radiated from the illuminating device 100. In the case of the endoscopic system according to the present embodiment, the optical system 210 is configured to be capable of taking in the illumination light via an observation window attached to the tip of the endoscope probe.

The light receiving unit 230 includes a solid-state imaging element such as a charge coupled device (CCD) and a complementary metal oxide semiconductor (CMOS), for example. The light receiving unit 230 is disposed at an imaging position of the optical system 210, and a subject image of the imaging target 400 is captured by the illumination light radiated to and reflected by the imaging target 400. The light receiving unit 230 generates an image signal by the photoelectric conversion of the captured subject image, and outputs the generated image signal to the imaging processing unit 250.

The imaging processing unit 250 includes a CPU and a storage element, generates an image on the basis of the image signal output from the light receiving unit 230, and displays the image on an un-illustrated monitor, or the like. At this time, the imaging processing unit 250 detects the luminance of the whole image or each pixel included in a preliminarily determined region. Furthermore, the imaging processing unit 250 calculates an average value of the luminance values detected in respective pixels, and outputs the calculated average value of the luminance values to the red light source control unit 110R, the green light source control unit 110G, and the blue light source control unit 110B in the illuminating device 100. At this time, in the endoscopic system according to the present embodiment, the luminance value detected by the light receiving unit 230 can be different depending on an individual difference of the endoscope probe.

1.2. Control Processing Example of Illuminating Device

In the above, the overall configuration example of the image acquisition system 10 according to the present embodiment has been explained. Next, there will be explained control processing of the illuminating device 100 in the image acquisition system 10 according to the present embodiment.

1.2.1. White Balance Adjustment Processing Example

Figure 4:
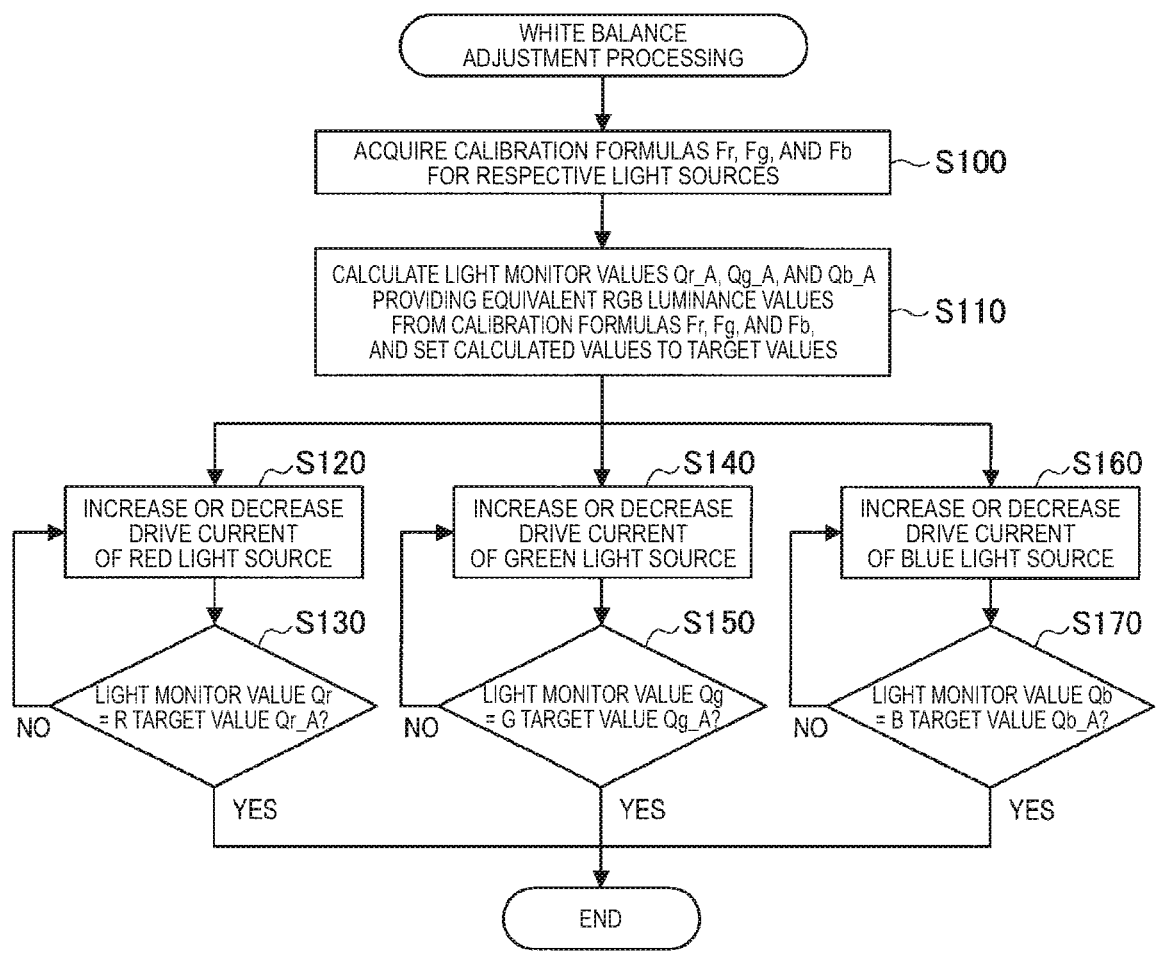
FIG. 4 is a flowchart illustrating an example of white balance adjustment processing.

FIG. 4 illustrates a flowchart of a white balance adjustment processing example in the illuminating device 100 according to the present embodiment. This white balance adjustment processing flow is started when an un-illustrated white balance adjustment processing start button is pressed down by a user, for example.

First, in step S100, the red light source control unit 110R, the green light source control unit 110G, and the blue light source control unit 110B calculate the correlations between the light amounts of the emission light beams (light monitor values) Qr, Qg, and Qb and the luminance values Lr, Lg, and Lb for the red light, the green light, and the blue light, respectively. In the present embodiment, calibration formulas Fr, Fg, and Fb are calculated expressing the correlations between the light amounts (light monitor values) Qr, Qg, and Qb of the emission light beams from the red light source 130R, the green light source 130G, and the blue light source 130B and the luminance values Lr, Lg, and Lb detected by the light receiving unit 230, respectively. The calculation of such calibration formulas Fr, Fg, and Fb may be performed in the stage of attaching the endoscope probe to the illuminating device 100 when the endoscopic system is started to be used, for example. By the calculation of such calibration formulas Fr, Fg, and Fb, the light amounts Qr, Qg, and Qb of the emission light beams from the respective light sources and the luminance values Lr, Lg, and Lb detected by the light receiving unit 230 are associated with each other respectively after the individual difference of the endoscope probe to be used is adjusted.

Figure 5:
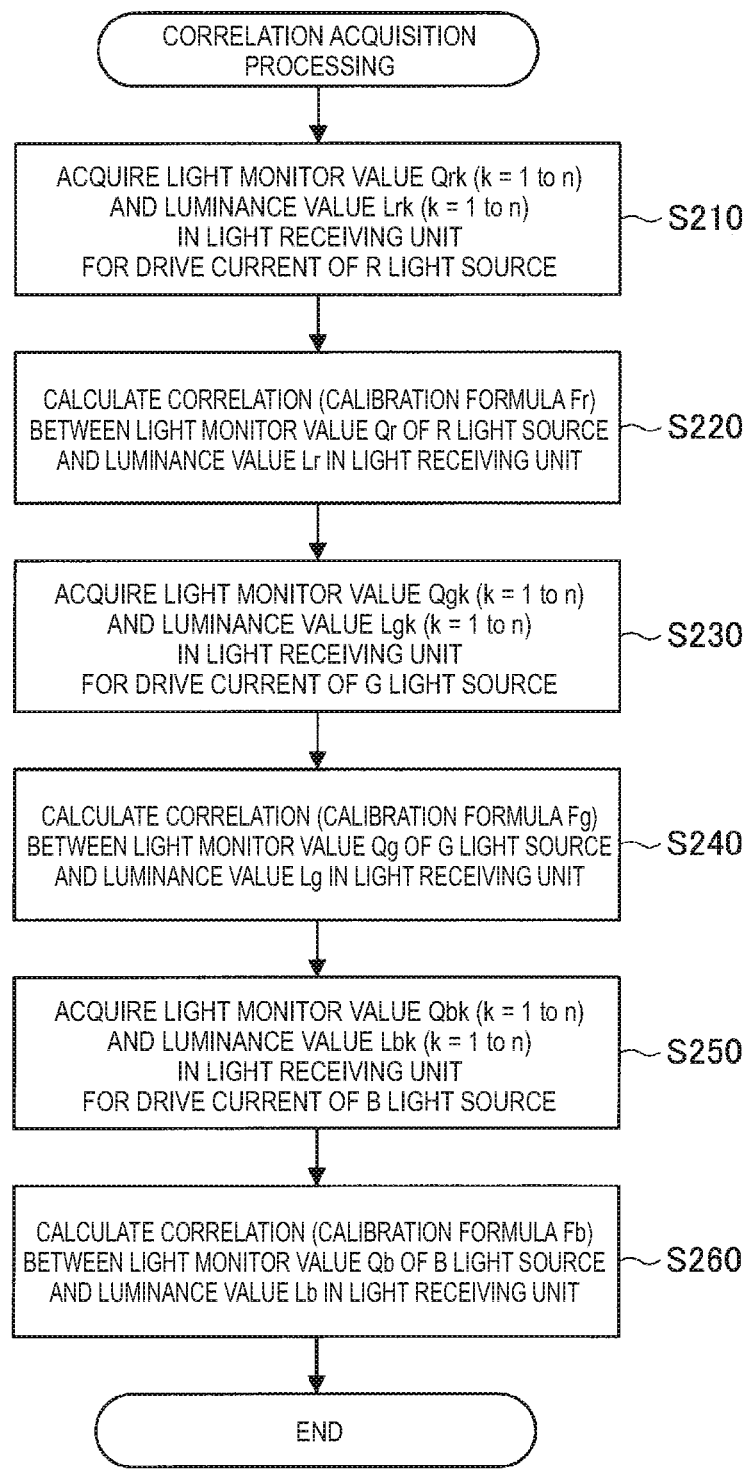
FIG. 5 is a flowchart illustrating an example of correlation acquisition processing.

FIG. 5 illustrates a flowchart of correlation acquisition processing by the illuminating device 100. In the case of the endoscopic system according to the present embodiment, the following correlation acquisition processing is carried out under the condition that a cover is attached to the tip of the endoscope probe, for example, so as to image a white subject as a reference. Except for the case that the cover is attached to the tip of the endoscope probe, the correlation acquisition processing may be performed while imaging a preliminarily determined white subject.

First, in step S210, for the red light, the red light source control unit 110R measures the light monitor value (voltage value: V) with respect to the drive current of the red light source 130R and the luminance value detected by the light receiving unit 230. Specifically, the red light source control unit 110R causes the red light to be emitted while changing the drive current supplied to the red light source 130R in the state without causing the green light and the blue light to be emitted. In this state, the red light source control unit 110R acquires the light monitor value $Qr_k$ (k=1 to n) detected by the red light monitor unit 150R and the luminance value $Lr_k$ (k=1 to n) detected by the light receiving unit 230 for a plurality of drive current values $A_k$ (k=1 to n).

Next, in step S220, the red light source control unit 110R calculates the calibration formula Fr expressing the correlation for the red light between the light monitor value Qr and the luminance value Lr on the basis of the acquired light monitor value $Qr_k$ (k=1 to n) and luminance value $Lr_k$ (k=1 to n). While a quadratic polynomial can be used for the calibration formula, for example, the calculation method of the calibration formula and the order of the calibration formula can be set arbitrarily.

After the calculation of the calibration formula Fr for the red light source 130R, subsequently in step S230, the green light source control unit 110G measures the light monitor value (V) with respect to the drive current of the green light source 130G and the luminance value detected by the light receiving unit 230. Such measurement is performed while changing the drive current supplied to the green light source 130G in the state without causing the red light and the blue light to be emitted. Subsequently, in step S240, the green light source control unit 110G calculates the calibration formula Fg expressing the correlation for the green light on the basis of the acquired light monitor value $Qg_k$ (k=1 to n) and luminance value $Lg_k$ (k=1 to n).

After the calculation of the calibration formula Fg for the green light source 130G, subsequently in step S250, the blue light source control unit 110B measures the light monitor value (V) with respect to the drive current of the blue light source 130B and the luminance value detected by the light receiving unit 230. Such measurement is performed while changing the drive current supplied to the blue light source 130B in the state without causing the red light and the green light to be emitted. Next, in step S260, the blue light source control unit 110B calculates the calibration formula Fb expressing the correlation for the blue light on the basis of the acquired light monitor value $Qb_k$ (k=1 to n) and luminance value $Lb_k$ (k=1 to n).

Figure 6:
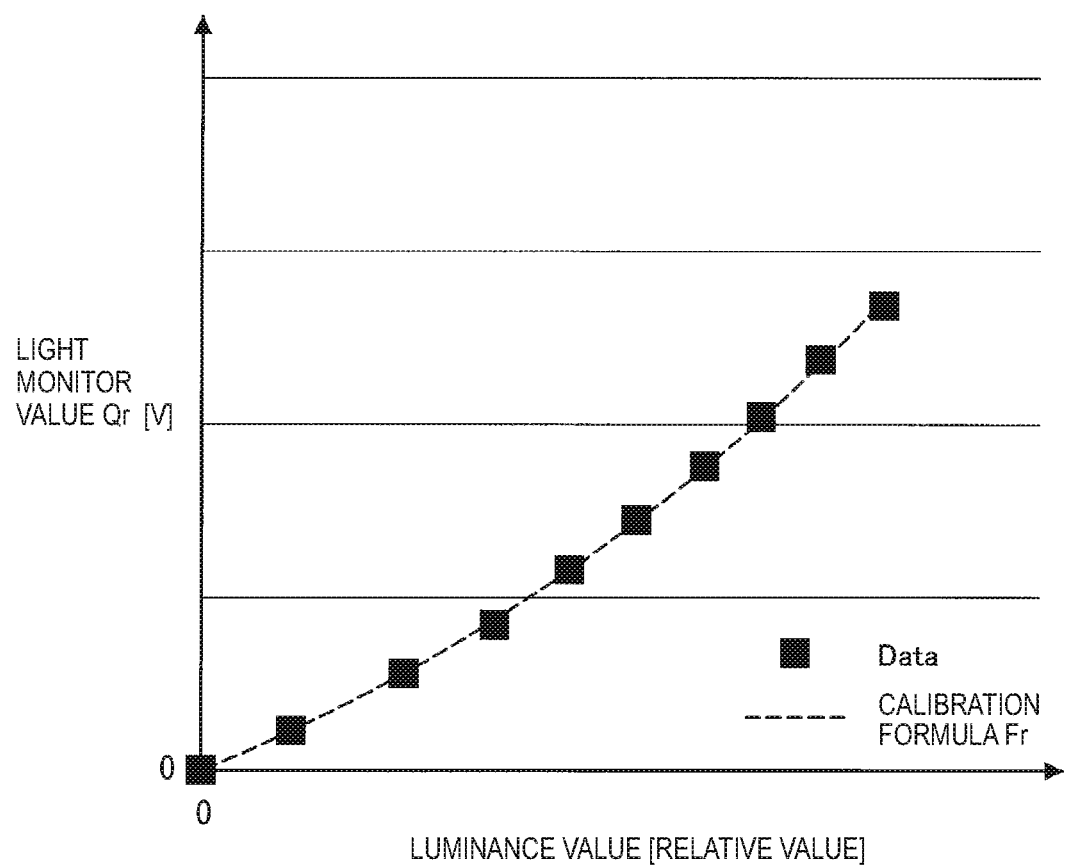
FIG. 6 is a diagram illustrating a correlation between a light amount detection value of a red light source and a luminance value of a light receiving unit.
Figure 7:
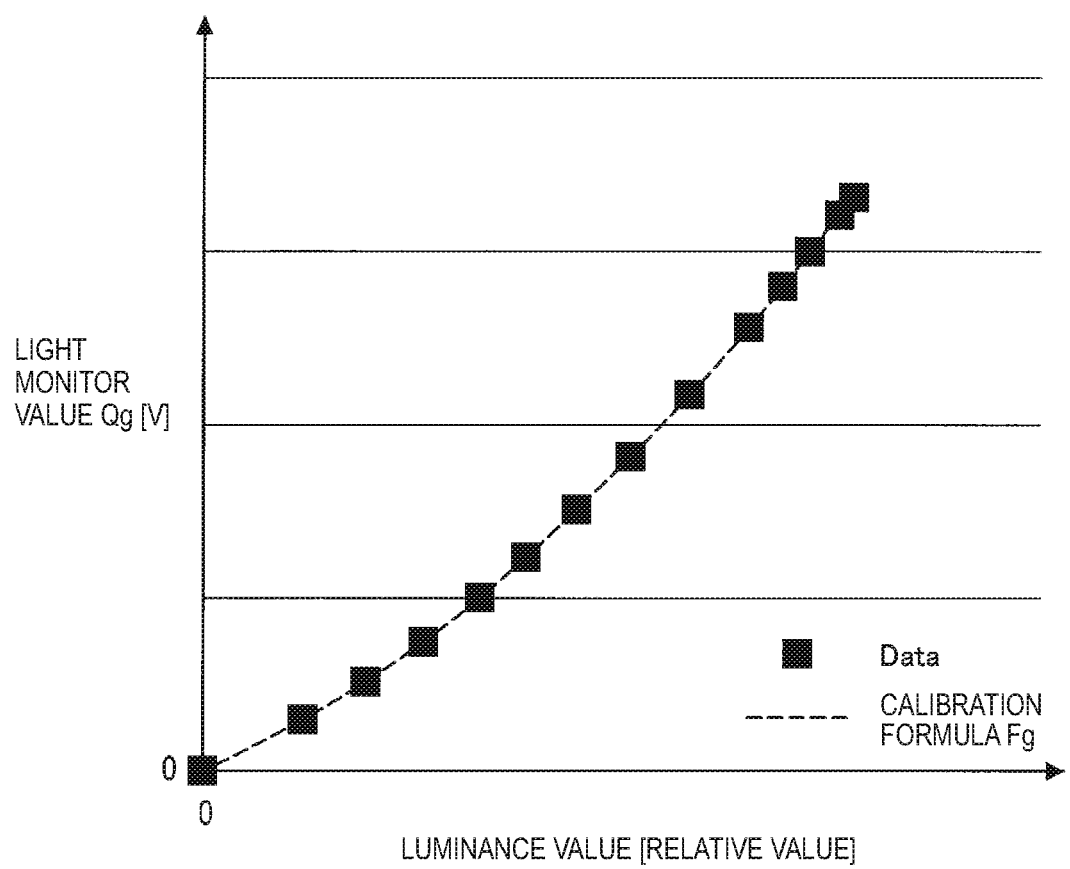
FIG. 7 is a diagram illustrating a correlation between a light amount detection value of a green light source and a luminance value of a light receiving unit.
Figure 8:
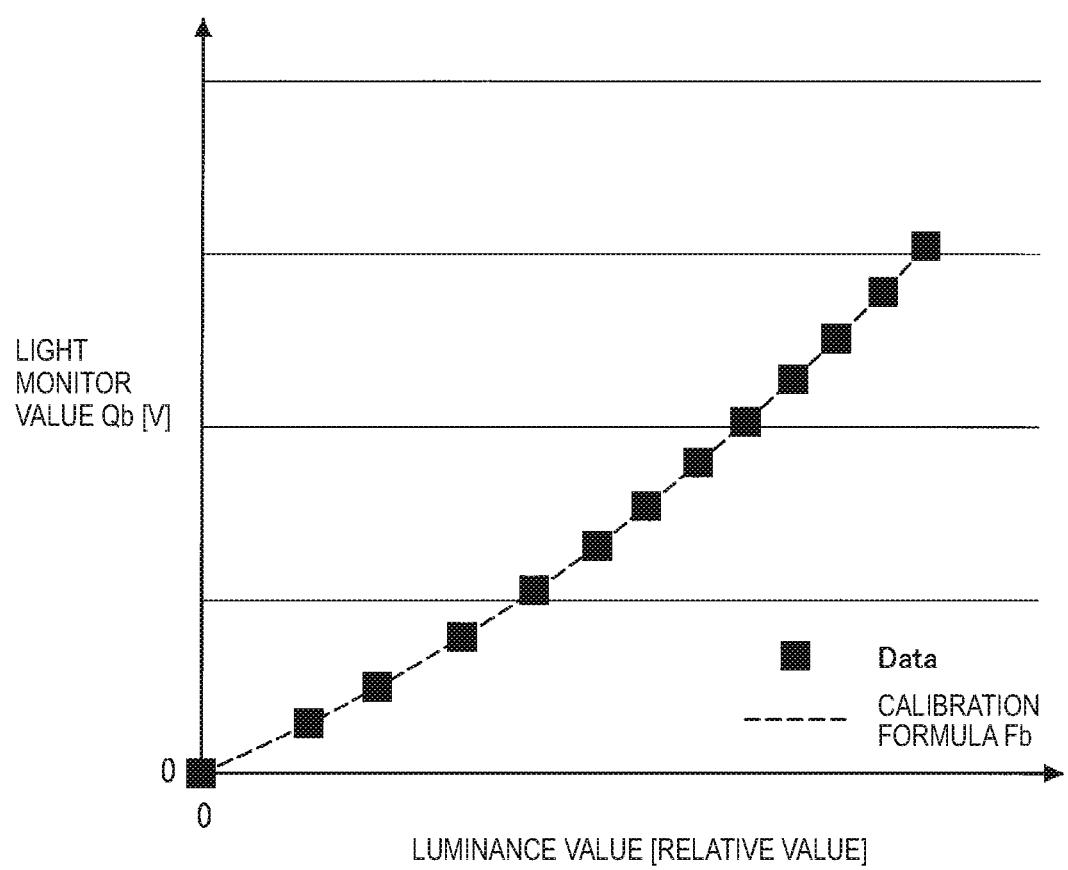
FIG. 8 is a diagram illustrating a correlation between a light amount detection value of a blue light source and a luminance value of a light receiving unit.

FIG. 6 to FIG. 8 illustrate the correlations between the light monitor values detected by the photodiodes and the luminance values detected by the CCDs which are acquired in the above described correlation acquisition processing sequences for the red light, green light, and the blue light, respectively. Each of FIG. 6 to FIG. 8 has the same scale in the vertical axis and the horizontal axis. In the illustrated example, the gradients of the calibration formulas Fr, Fg, and Fb calculated from data acquired for the respective color light beams have the smallest value for the red light, the larger value for the blue light, and the largest value for the green light. That is, for the respective color light beams, the magnitudes of the light amounts Qr, Qg, and Qb to cause the luminance values Lr, Lg, and Lb detected by the light receiving unit 230 to be the same have the smallest value for the red light, the larger value for the blue light, and the largest value for the green light.

Note that, while, in the correlation acquisition processing illustrated in FIG. 5, the calibration formulas Fr, Fg, and Fb are calculated in the order of the red light, the green light, and the blue light, the order may be changed arbitrarily. Further, the calibration formulas Fr, Fg, and Fb may be calculated for the respective color light beams after the acquisition of the light monitor values and the luminance values for all the light sources of the three colors.

Returning to FIG. 4, after the acquisition of the calibration formulas Fr, Fg, and Fb for the light beams emitted from the respective light sources in step S100, the process proceeds to step S110. In step S110, the red light source control unit 110R, the green light source control unit 110G, and the blue light source control unit 110B calculate light monitor values Qr_A, Qg_A, and Qb_A with which the respective color light beams provide the same luminance value L0 that is preliminarily set, on the basis of the calibration formulas Fr, Fg, and Fb, respectively. Then, the respective control units set the calculated values Qr_A, Qg_A, and Qb_A to target values for the drive control of the light sources, respectively. For example, the respective control units calculate light monitor values to provide a luminance value of 200 on the basis of the calibration formulas Fr, Fg, and Fb, and set the light monitor values to the target values for the drive control of the light sources, respectively.

Next, the red light source control unit 110R increases or decreases the drive current of the red light source 130R in step S120. Subsequently, the red light source control unit 110R determines whether or not the light monitor value Qr detected by the red light monitor unit 150R has become the target value Qr_A set in step S110, in step S130. The red light source control unit 110R repeats the processing of step S120 to step S130 until the detected light monitor value Qr becomes the target value Qr_A. Similarly, also the green light source control unit 110G and the blue light source control unit 110B repeat the increase or decrease of the drive currents and the determinations until the light monitor values Qg and Qb detected by the green light monitor unit 150G and the blue light monitor unit 150B become the target values Qg_A and Qb_A set in step S110 (step S140 to step S150 and step S160 to step S170), respectively.

When the light monitor values Qr, Qg, and Qb coincide with the target values Qr, Qg_A, and Qb_A for all of the red light, the green light, and the blue light, the white balance adjustment processing is finished. In this manner, the endoscopic system according to the present embodiment can perform the white balance adjustment easily without observing the image captured by the imaging processing device 200 after once having acquired the calibration formulas Fr, Fg, and Fb between the respective light monitor values and luminance values for the color light beams.

1.2.2. Color Temperature Adjustment Processing Example

Figure 9:
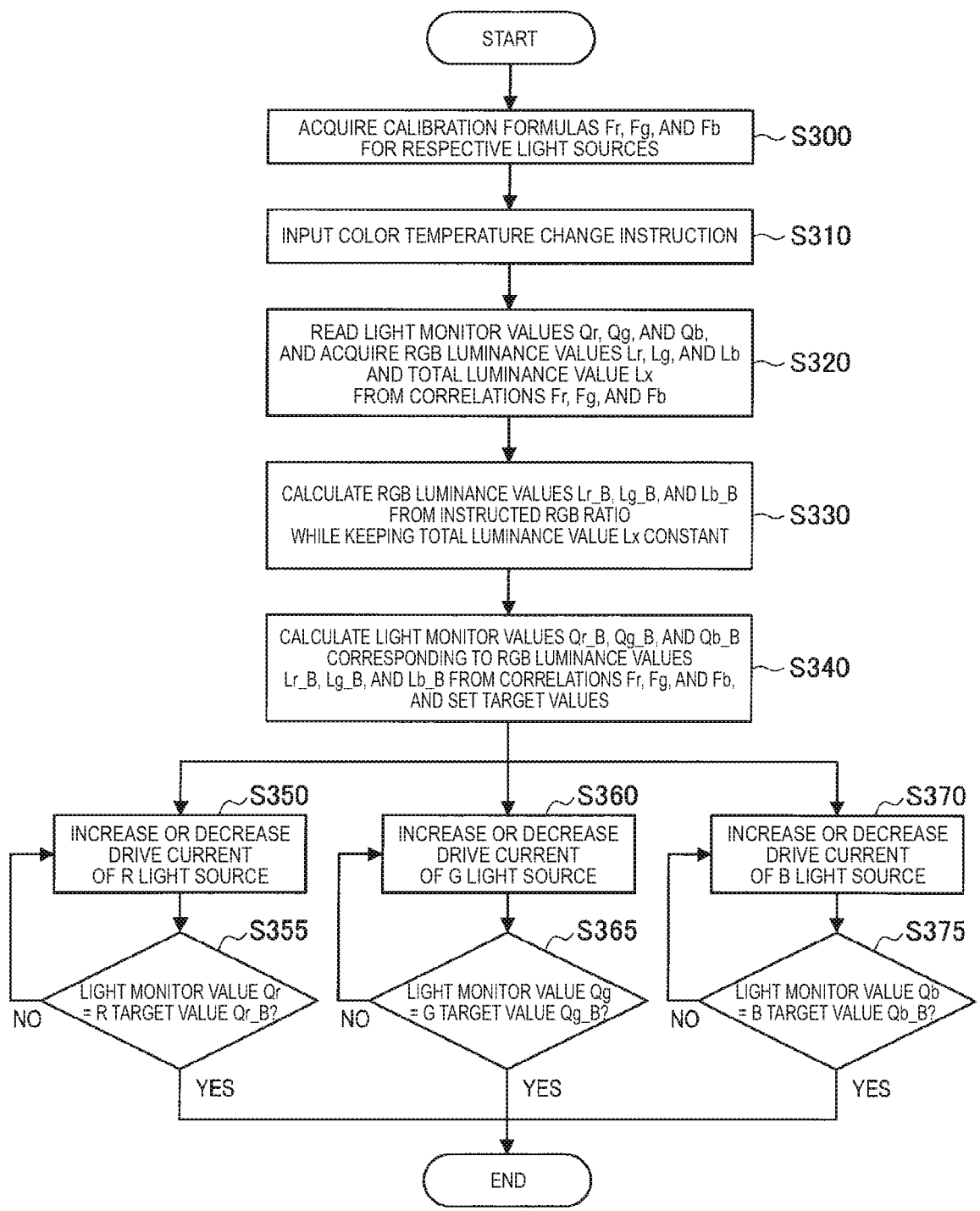
FIG. 9 is a flowchart illustrating an example of light amount adjustment processing.

FIG. 9 illustrates a flowchart of a color temperature adjustment processing example in the illuminating device 100 according to the present embodiment. This color temperature adjustment processing flow is a processing flow to adjust the color temperature of the illumination light by changing the luminance ratio of the red light, the green light, and the blue light (RGB ratio) while maintaining the light amount Qx of the currently radiated illumination light.

First, in step S300, the red light source control unit 110R, the green light source control unit 110G, and the blue light source control unit 110B calculate the correlations between the light amounts Qr, Qg, and Qb and the luminance values Lr, Lg, and Lb for the emission light beams of the red light, green light, and the blue light, respectively. In the present embodiment, the calibration formulas Fr, Fg, and Fb are calculated to express the correlations between the light amounts Qr, Qg, and Qb and the luminance values Lr, Lg, and Lb for the emission light beams, respectively. This step S300 is performed in the sequence exemplified in FIG. 5 similarly to the white balance adjustment processing step S100 illustrated in FIG. 4, and may be performed preferably in the stage when the endoscope probe is attached to the illuminating device 100.

Next, in step S310, each of the red light source control unit 110R, the green light source control unit 110G, and the blue light source control unit 110B receives the input of an instruction to change the color temperature of the illumination light. Subsequently, in step S320, the respective control units read the light monitor values Qr, Qg, and Qb detected by the red light monitor unit 150R, the green light monitor unit 150G, and the blue light monitor unit 150B, respectively. Each of the control units may be configured to exchange the information of the light monitor values Qr, Qg, and Qb, or each of the control units may read all the light monitor values Qr, Qg, and Qb.

Then, the luminance values Lr, Lg, and Lb corresponding to the light monitor values Qr, Qg, and Qb and a total luminance value Lx are calculated for the light beams of the three colors on the basis of the calculated calibration formulas Fr, Fg, and Fb, respectively. The instruction to change the color temperature in step S310 is input by RGB ratio setting by a user or the press down of an un-illustrated input switch in which an RGB ratio is preliminarily set, for example. Further, the calculation of the total luminance value Lx in step S320 may be performed in any control unit of the red light source control unit 110R, the green light source control unit 110G, and the blue light source control unit 110B, and the total luminance value Lx may be output to the other control units.

Next, in step S330, the red light source control unit 110R, the green light source control unit 110G, and the blue light source control unit 110B calculate respective luminance values Lr_B, Lg_B, and Lb_B of the colors on the basis of the instructed RGB ratio while maintaining the total luminance value Lx.

Next, in step S340, the red light source control unit 110R calculates a light monitor value Qr_B with which the red light provides the luminance value Lr_B calculated in step S330, on the basis of the calibration formula Fr acquired in step S300. Similarly, the green light source control unit 110G and the blue light source control unit 110B calculate light monitor values Qg_B and Qb_B with which the respective color light beams provide the luminance values Lg_B and Lb_B calculated in step S330, on the basis of the calibration formulas Fg and Fb acquired in step S300, respectively. Then, the respective control units set the calculated values Qr_B, Qg_B, and Qb_B to target values for the drive control of the light sources, respectively.

Next, the red light source control unit 110R increases or decreases the drive current of the red light source 130R in step S350. Subsequently, the red light source control unit 110R determines whether or not the light monitor value Qr detected by the red light monitor unit 150R in step S355 has become the target value Qr_B set in step S340. The red light source control unit 110R repeats the processing of step S350 to step S355 until the detected light monitor value Qr becomes the target value Qr_B. Similarly, also the green light source control unit 110G and the blue light source control unit 110B repeat the increase or decrease of the drive currents and the determinations until the light monitor values Qg and Qb detected by the green light monitor unit 150G and the blue light monitor unit 150B become the target values Qg_B and Qb_B set in step S340 (step S360 to step S365 and step S370 to step S375), respectively.

When the light monitor values Qr, Qg, and Qb coincide with the target values Qr_B, Qg_B, and Qb_B for all the red light, the green light, and the blue light, respectively, the color temperature adjustment processing is finished. As a result, it is possible to adjust the color temperature of the illumination light to a color temperature set by the user or a preliminarily set color temperature while maintaining the light amount of the illumination light. In this manner, the endoscopic system according to the present embodiment acquires the calibration formulas Fr, Fg, and Fb expressing the correlations between the light monitor values Qr, Qg, and Qb and the luminance values Lr, Lg, and Lb for the color light beams, respectively, after the attachment of the endoscope probe, for example. Thereby, in usage after that, it is possible to perform the adjustment of the color temperature while maintaining the light amount Qx of the illumination light, without observing the image captured by the imaging processing device 200.

1.2.3. Light Amount Adjustment Processing Example

Figure 10:
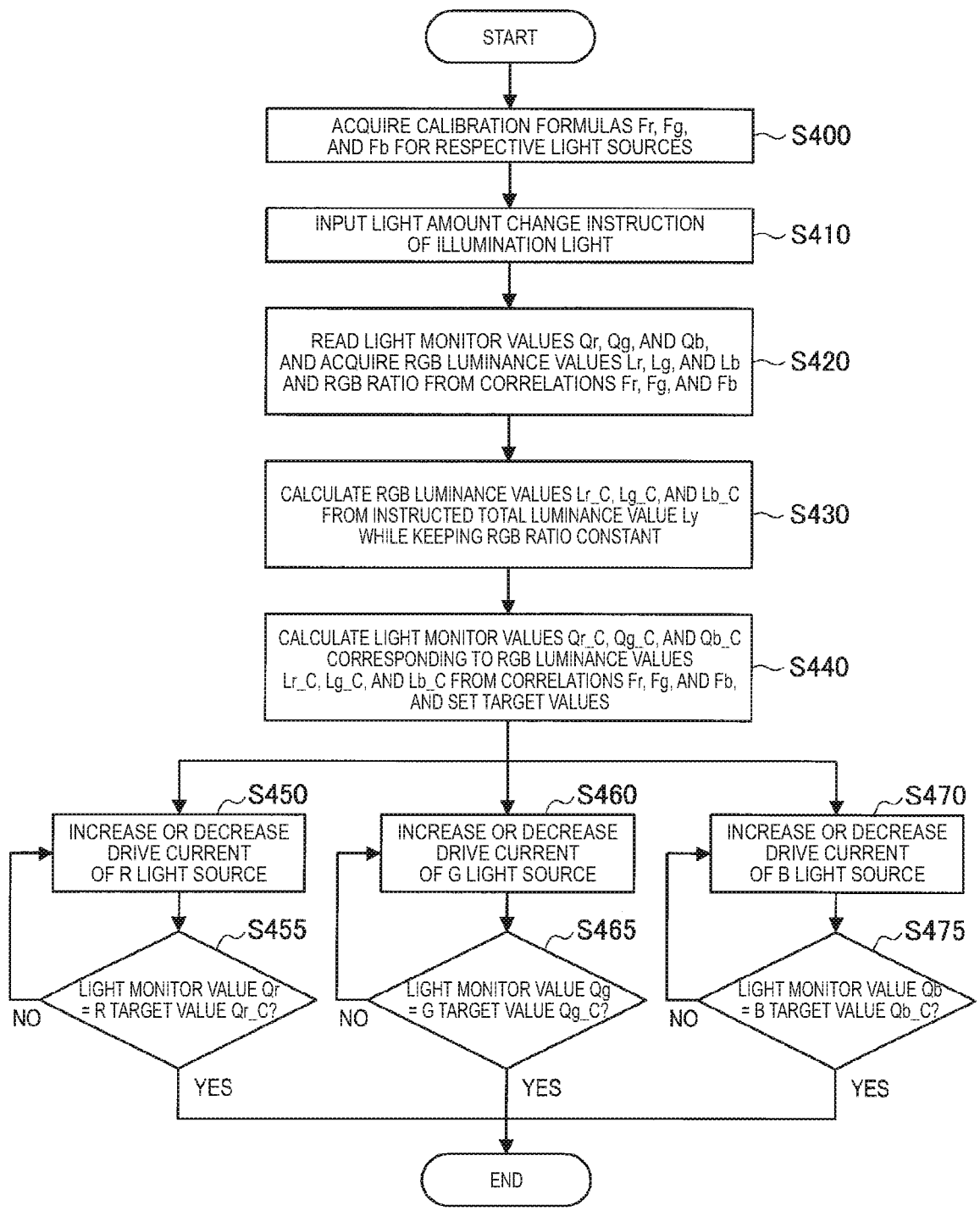
FIG. 10 is a flowchart illustrating an example of color temperature adjustment processing.

FIG. 10 illustrates a flowchart of a light amount adjustment processing example by the illuminating device 100 according to the present embodiment. This light amount adjustment processing flow is a processing flow to adjust the light amount of the illumination light by changing the light amounts of the red light, the green light, and the blue light while maintaining the color temperature of the currently radiated illumination light, that is, the luminance ratio of the red light, the green light, and the blue light (RGB ratio).

First, in step S400, for the red light, the red light source control unit 110R calculates the calibration formula Fr expressing the correlation between the light amount Qr of the emission light beams from the red light source 130R and the luminance value Lr detected by the light receiving unit 230. Similarly, the green light source control unit 110G and the blue light source control unit 110B calculate the calibration formulas Fg and Fb expressing the correlations between the light amounts of the emission light beams Qg and Qb and the luminance values Lg and Lb for the green light and the blue light, respectively. This step S400 is performed in the sequence exemplified in FIG. 5 as the white balance adjustment processing step S100 illustrated in FIG. 4, and may be performed in the stage when the endoscope probe is attached to the illuminating device 100.

Next, in step S410, each of the red light source control unit 110R, the green light source control unit 110G, and the blue light source control unit 110B receives the input of an instruction to change the light amount of the illumination light. Subsequently, in step S420, the respective control units read the light monitor values Qr, Qg, and Qb detected by the red light monitor unit 150R, the green light monitor unit 150G, and blue light monitor unit 150B, respectively. Each of the control units may be configured to exchange the information of the light monitor values Qr, Qg, and Qb, or each of the controls unit may be configured to read all the light monitor values Qr, Qg, and Qb.

Then, the respective control units calculate the luminance values Lr, Lg, and Lb corresponding to the light monitor values Qr, Qg, and Qb and the luminance ratio for the light beams of the three colors on the basis of the calculated calibration formulas Fr, Fg, and Fb, respectively. The instruction to change the light amount in step S410 is input by the adjustment of a light amount adjustment dial by the user, or the press down of an un-illustrated switch in which the light amount is set preliminarily, for example. Further, the calculation of the luminance ratio in step S420 may be performed in any of the red light source control unit 110R, the green light source control unit 110G, and the blue light source control unit 110B, and the luminance ratio may be output to the other control units.

Next, in step S430, the red light source control unit 110R calculates a luminance value Lr_C of the red light so as to cause the total luminance value of the red light, the green light, and the blue light to become a luminance value Ly corresponding to the instructed light amount of the illumination light while maintaining the luminance ratio. Similarly, the green light source control unit 110G and the blue light source control unit 110B calculate luminance values Lg_C and Lb_C of the respective color light beams so as to cause the total luminance value of the respective color light beams to become a luminance value Ly corresponding to the instructed light amount of the illumination light while maintaining the luminance ratio.

Next, in step S440, the red light source control unit 110R calculates a light monitor value Qr_C with which the red light provides the luminance value Lr_C calculated in step S430, on the basis of the calibration formula Fr acquired in step S400. Similarly, the green light source control unit 110G and the blue light source control unit 110B calculate light monitor values Qg_C and Qb_C with which the respective color light beams provide the luminance values Lg_C and Lb_C calculated in step S430, on the basis of the calibration formulas Fg and Fb acquired in step S400, respectively. Then, the respective control units set the calculated values Qr_C, Qg_C and Qb_C to target values of the drive control in the light sources, respectively.

Next, the red light source control unit 110R increases or decreases the drive current of the red light source 130R in step S450. Subsequently, the red light source control unit 110R determines whether or not the light monitor value Qr detected by the red light monitor unit 150R in step S455 has become the target value Qr_C set in step S440. The red light source control unit 110R repeats the processing in step S450 to step S455 until the detected monitor value Qr becomes the target value Qr_C. Similarly, the green light source control unit 110G and the blue light source control unit 110B also repeat the increase or decrease of the drive currents and the determinations until the light monitor values Qg and Qb detected by the green light monitor unit 150G and the blue light monitor unit 150B become the target values Qg_C and Qb_C set in step S440 (step S460 to step S465 and step S470 to step S475), respectively.

When the light monitor values Qr, Qg, and Qb coincide with the target values Qr_C, Qg_C, and Qb_C in all of the red light, the green light, and the blue light, the light amount adjustment processing of the illumination light is finished. As a result, it is possible to adjust the light amount of the illumination light to a light amount set by the user or set preliminarily while maintaining the color temperature of the illumination light. In this manner, the endoscopic system according to the present embodiment calculates the calibration formulas Fr, Fg, and Fb expressing the correlations between the light monitor values Qr, Qg, and Qb and the luminance values Lr, Lg, and Lb for the color light beams when the endoscope probe is attached, for example. Thereby, in usage after that, it is possible to perform the adjustment of the light amount easily while maintaining the color temperature of the illumination light without observing the image captured by the imaging processing device 200.

As explained above, in the illuminating device 100 and the image acquisition system 10 according to the first embodiment of the present disclosure, the light amount of the red light emitted from the red light source 130R is detected by the red light monitor unit 150R as the light monitor value Qr. Similarly, in the illuminating device 100 and the image acquisition system 10, the light amounts of the green light and the blue light emitted from the green light source 130G and the blue light source 130B are detected by the green light monitor unit 150G and the blue light monitor unit 150B as the light monitor values Qr, Qg, and Qb, respectively.

Further, in the illuminating device 100 and the image acquisition system 10 according to the present embodiment, the red light source control unit 110R, the green light source control unit 110G, and the blue light source control unit 110B receive the luminance values Lr, Lg, and Lb detected by the light receiving unit 230 of the imaging processing device 200, together with the light monitor values Qr, Qg, and Qb, respectively. Then, each of the illuminating device 100 and the image acquisition system 10 acquires the calibration formulas Fr, Fg, and Fb expressing the correlations between the luminance value Lr, Lg, and Lb and the light monitor values Qr, Qg, and Qb, respectively.

Accordingly, each of the illuminating device 100 and the image acquisition system 10 according to the present embodiment can adjust the color temperature of the illumination light accurately by adjusting the light amounts of the light sources on the basis of the respective calibration formulas Fr, Fg, and Fb. Thereby, it is not necessary to adjust the gain of the light receiving unit 230 of the imaging processing device 200, and therefore it is possible to reduce electronic noise and capture an image having a good quality. Further, it is possible to reduce power consumption in each of the light sources by adjusting the light amount in each of the light sources and thereby adjusting the color temperature of the illumination light without adjusting the gain of the light receiving unit 230. Further, it is possible to adjust the color temperature of the illumination light accurately by adjusting the light amount in each of the light sources and thereby adjusting the color temperature of the illumination light without adjusting the gain of the light receiving unit 230, without observing the image captured by the imaging processing device 200 at each time.

Further, each of the illuminating device 100 and the image acquisition system 10 according to the present embodiment acquires the calibration formulas Fr, Fg, and Fb expressing the correlations between the light monitor values Qr, Qg, and Qb and the luminance values Lr, Lg, and Lb detected by the light receiving unit 230, respectively, once when the endoscope probe is attached, for example. Thereby, after that, it is possible to adjust the color temperature of the illumination light easily without considering the effect of the endoscope probe as long as using the same endoscope probe.

Furthermore, even in the case of using a different endoscope probe, it is possible to adjust the color temperature of the illumination light accurately by acquiring the calibration formulas Fr, Fg, and Fb when the endoscope probe is attached. Accordingly, without depending on the individual difference of the endoscope probe, it is possible to capture a desired image suitable for an imaging object in the endoscopic system used in a medical front, for example.

Further, each of the illuminating device 100 and the image acquisition system 10 according to the present embodiment acquires the calibration formulas Fr, Fg, and Fb expressing the correlations between the light monitor values Qr, Qg, and Qb and the luminance values Lr, Lg, and Lb detected by the light receiving unit 230, respectively. Thereby, it is possible to adjust the color temperature easily by changing the RGB ratio of the illumination light while keeping the light amount of the illumination light constant. Further, since the calibration formulas Fr, Fg, and Fb are acquired as above, it is possible to change the light amount of the illumination light easily while keeping the color temperature of the illumination light constant.

2. Second Embodiment

A second embodiment of the present disclosure is different from the first embodiment in the point that a red light source, a green light source, and a blue light source are driven and controlled by a common control unit. In the following, the point different from the illuminating device of the first embodiment will be explained.

Figure 11:
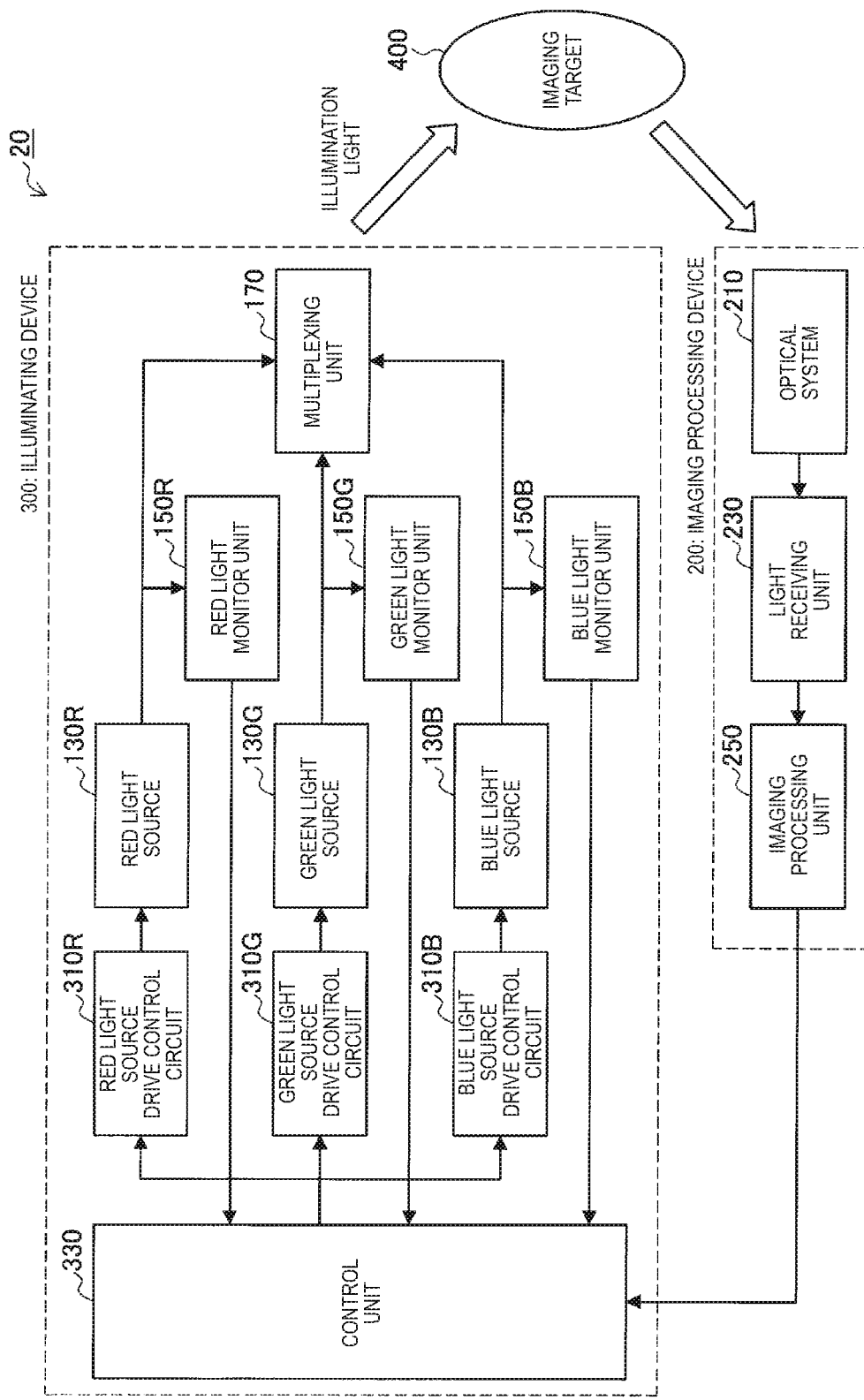
FIG. 11 is a block diagram illustrating an image acquisition system according to a second embodiment of the present disclosure.

FIG. 11 is a block diagram illustrating an overall configuration of an image acquisition system 20 according to the second embodiment of the present disclosure. Similarly to the image acquisition system 10 of the first embodiment, this image acquisition system 20 includes an illuminating device 300 and an imaging processing device 200 and is configured as an endoscopic system, for example.

In this configuration, the imaging processing device 200 can be configured similarly to the imaging processing device 200 of the image acquisition system 10 according to the first embodiment except the point that a signal is output from an imaging processing unit 250 to a control unit 330 of the illuminating device 300.

The illuminating device 300 includes a red light source 130R, a green light source 130G, a blue light source 130B, a red light source drive control circuit 310R, a green light source drive control circuit 310G, a blue light source drive control circuit 310B, the control unit 330, and a multiplexing unit 170. Further, the illuminating device 300 includes a red light monitor unit 150R, a green light monitor unit 150G, and a blue light monitor unit 150B.

The red light source 130R, the green light source 130G, and the blue light source 130B can be configured similarly to the light source in the illuminating device 100 according to the first embodiment. Further, the light source is not limited to the light sources for three colors R, G, and B and the number of light sources is not limited as in light sources for four colors or the like. The red light monitor unit 150R, the green light monitor unit 150G, and the blue light monitor unit 150B can be configured similarly to the respective monitor units of the illuminating device 100 according to the first embodiment except that detected light monitor values Qr, Qg, and Qb are transmitted to the control unit 330. Also the multiplexing unit 170 can be configured similarly to the multiplexing unit 170 of the illuminating device 100 exemplified in FIG. 3 according to the first embodiment.

The control unit 330 sets the drive currents of the light sources on the basis of the correlations between luminance values Lr, Lg, and Lb of the red light, the green light, and the blue light detected by the light receiving unit 230 of the imaging processing device 200 and the light monitor values Qr, Qg, and Qb detected by the light monitor units, respectively. Further, the control unit 330 transmits instructions to drive the red light source 130R, the green light source 130G, and the blue light source 130B to the red light source drive control circuit 310R, the green light source drive control circuit 310G, and the blue light source drive control circuit 310B on the basis of the set drive currents of the light sources, respectively. The red light source drive control circuit 310R, the green light source drive control circuit 310G, and the blue light source drive control circuit 310B drive the red light source 130R, the green light source 130G, and the blue light source 130B, respectively, on the basis of the drive instructions.

In the illuminating device 100 according to the first embodiment, the red light source control unit 110R, the green light source control unit 110G, and the blue light source control unit 110B receive the light monitor values Qr, Qg, and Qb and the luminance values Lr, Lg, and Lb and calculate the calibration formulas Fr, Fg, and Fb expressing the correlations, respectively. On the other side, in the illuminating device 300 according to the present embodiment, the common control unit 330 is configured to receive the light monitor values Qr, Qg, and Qb and the luminance values Lr, Lg, and Lb and to calculate the calibration formulas Fr, Fg, and Fb expressing the correlations between the light monitor values and the luminance values, respectively. The contents of a calculation method of such calibration formulas Fr, Fg, and Fb, and the contents of the white balance adjustment processing, color temperature adjustment processing, and the light amount adjustment processing to be performed by the control unit 330 can be carried out similarly to the illuminating device 100 according to the first embodiment.

The illuminating device 300 and the image acquisition system 20 according to the present embodiment can provide the same effect as the illuminating device 100 and the image acquisition system 10 according to the first embodiment. In addition, in the illuminating device 300 and the image acquisition system 20 according to the present embodiment, the target value calculation of the light monitor values in driving and controlling the respective light sources is performed by one control unit, and it is possible to reduce the load in the transmission and reception of the calculation results and the like between the control units. Note that, while the control unit 330 is provided in the illuminating device 300 in the example illustrated in FIG. 11, the control unit 330 may be provided as a control device separated from the illuminating device 300, and the imaging processing device 200 may include a control unit.

3. Third Embodiment

A third embodiment of the present disclosure is different from the first and second embodiments in the point that a control unit of each light source has a function as a deterioration determination unit to determine the deterioration of the light source. For example, each of the red light source control unit 110R, the green light source control unit 110G, and the blue light source control unit 110B according to the first embodiment and the control unit 330 according to the second embodiment may have a function of the deterioration determination unit to determine the deterioration of the light source.

An illuminating device and an image acquisition system according to the present embodiment can be configured basically the same as the illuminating devices 100 and 300 and the image acquisition systems 10 and 20 illustrated in FIG. 1 and FIG. 11, respectively. On the other side, each of the illuminating device and the image acquisition system according to the present embodiment has a function of determining the deterioration of the light source in which the light amount is reduced along the elapse of the use time even when the same current is supplied. In the following, the illuminating device and the image acquisition system according to the present embodiment will be explained with reference to FIG. 12 using the illuminating device 100 and the image acquisition system 10 illustrated in FIG. 1 as an example.

Figure 12:
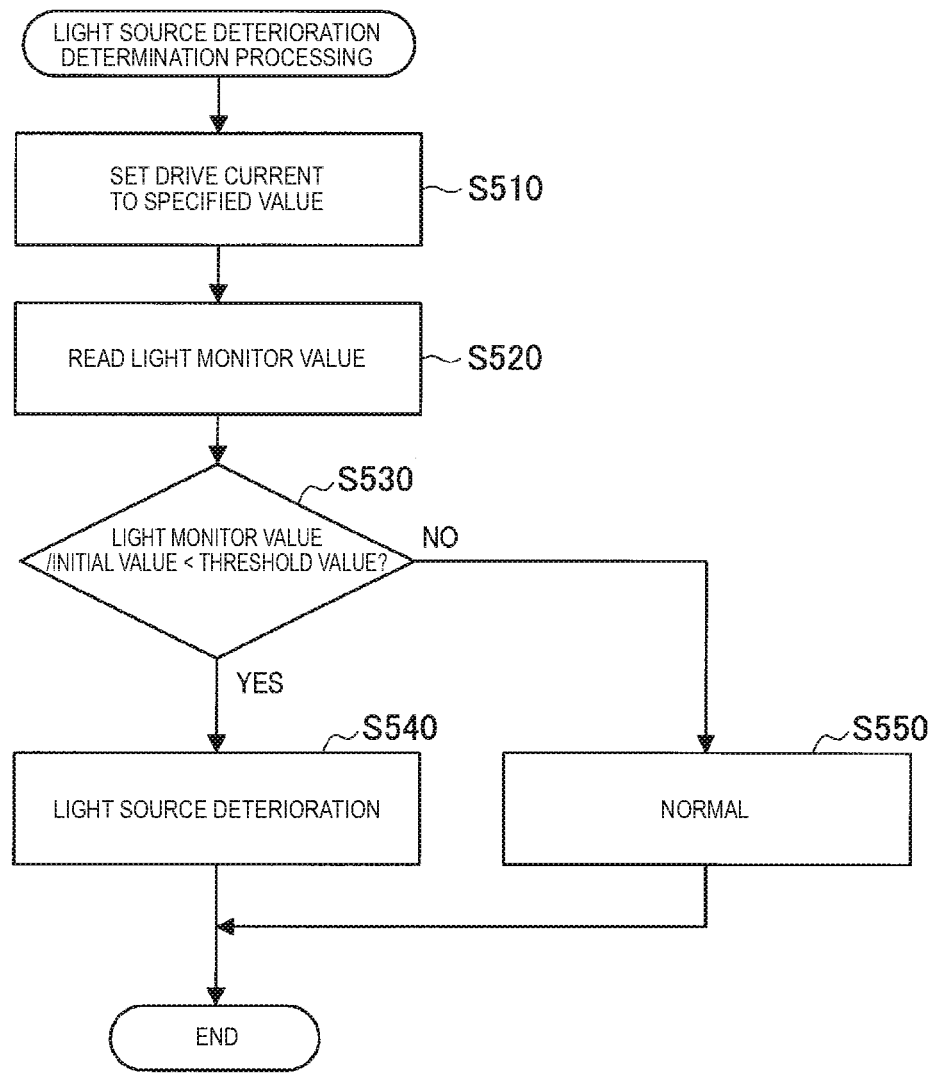
FIG. 12 is a flowchart illustrating an example of deterioration determination processing of a light source.

FIG. 12 is a flowchart illustrating a deterioration determination processing example of the light source. In the case of the illuminating device 100 illustrated in FIG. 1, the deterioration determination processing of each light source is carried out by the corresponding control unit. For example, explaining the deterioration determination of the red light source 130R, first in step S510, the red light source control unit 110R sets the drive current supplied to the red light source 130R to a preliminarily set specified value. Such a specified value may be set arbitrarily to a value which can detect the change of the light amount of the emission light beams emitted from the red light source 130R. Such a specified value is used as a common value when the deterioration determination of the red light source 130R is carried out. The same value may be set as the specified value for each of the light sources or the specified value may be different among the light sources.

Next, in S520, the red light source control unit 110R reads the light monitor value Qr detected by the red light monitor unit 150R in the state that the drive current having the specified value is supplied to the red light source 130R. Subsequently, the red light source control unit 110R determines whether or not the ratio R of the current light monitor value Qr to the initial value Qr0 of the light monitor value detected when the current having the same specified value is supplied to the red light source 130R at the use start is smaller than a preliminarily determined threshold value R0. If the ratio R is not smaller than the threshold value R0 (No in S530), the process proceeds to step S550, and the red light source control unit 110R determines that there is no deterioration in the red light source 130R and the process is finished. On the other side, if the ratio R is smaller than the threshold value R0 (Yes in S530), the process proceeds to step S540, and the red light source control unit 110R determines that the red light source 130R is deteriorated and the process is finished.

In the case of the illuminating device 100 illustrated in FIG. 1, also the green light source control unit 110G and the blue light source control unit 110B can carry out the deterioration determination processing of the green light source 130G and the blue light source 130B, respectively, in similar sequences. Further, in the case of the illuminating device 300 illustrated in FIG. 11, the control unit 330 can carry out the deterioration determination of each of the light sources sequentially along the sequence illustrated in FIG. 12.

Each of the above explained illuminating devices and the image acquisition systems according to the present embodiments includes the light monitor units 150 R, 150G, and 150B to detect the light amounts of the emission light beams emitted from the light sources, respectively Accordingly, the control units can determine the deterioration of the light sources on the basis of the reduction ratios of the light monitor values Qr, Qg, and Qb in the state that the same drive currents are supplied to the light sources, respectively.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, while the above embodiments assume that the luminance value L0 for acquiring the light monitor values Qr_A, Qg_A, and Qb_A which provide the same luminance value in the color light beams is preliminarily set in the white balance adjustment processing, the present technique is not limited to such an example. For example, a user may set an arbitrary luminance value L0 in the white balance adjustment processing.

Further, while, in the above embodiments, each of the red light source control unit, the green light source control unit, and the blue light source control unit or the control unit calculates the calibration formula, the present technique is not limited to such an example. For example, a calculation processing unit to calculate the calibration formula may be a device separate from each of the control units.

Further, while, in the above embodiments, each of the control units 110R, 110G, 110B, or 330 increases or decreases the drive current after the target light monitor value is acquired, the present technique is not limited to such an example. For example, after the target light monitor value is acquired, a user may adjust the drive current in each of the light sources.

Further, while, in the above embodiments, when the color temperature adjustment processing and the light amount adjustment processing are carried out, the color temperature is adjusted while the light amount of the illumination light is maintained, or the light amount is adjusted while the color temperature of the illumination light is maintained, the present technique is not limited to such an example. For example, the light amount in each of the light sources can be adjusted so as to cause both of the color temperature (RGB ratio) and the light amount of the illumination light to become respective set target values. In this case, a luminance value in each of the color light beams may be acquired on the basis of a total luminance value corresponding to the set light amount and the set RGB ratio, and a light monitor value corresponding to the luminance value may be set to the target value. Thereby, it is possible to adjust the light amount and the color temperature of the illumination light by adjusting the light amount in each of the color light beams.

Further, the effects described in this specification are merely illustrative or exemplified effects, and are not limitative. That is, with or in the place of the above effects, the technology according to the present disclosure may achieve other effects that are clear to those skilled in the art based on the description of this specification.

Additionally, the present technology may also be configured as below.

(1)
An illuminating device including:
a plurality of light sources;
a light monitor unit configured to detect each of light amounts of emission light beams emitted from the light sources; and
a control unit configured to control the light amounts of the emission light beams on the basis of a correlation between luminance acquired from a light receiving unit and the light amounts of the emission light beams.

(2)
The illuminating device according to (1), wherein
the control unit is configured to calculate the correlation.

(3)
The illuminating device according to (1) or (2), wherein
the plurality of light sources include a red light source, a green light source, and a blue light source.

(4)
The illuminating device according to any one of (1) to (3), wherein
the plurality of light sources are laser light sources.

(5)
The illuminating device according to any one of (1) to (4), including:
a deterioration determination unit configured to determine deteriorations in the light sources on the basis of the light amounts detected by the light monitor unit.

(6)
A control method for an illuminating device, the control method including:
a step of detecting each of light amounts of emission light beams emitted from a plurality of light sources; and
a step of controlling the light amounts of the emission light beams from the plurality of light sources on the basis of a correlation between luminance acquired from a light receiving unit and the light amounts of the emission light beams.

(7)

The control method for an illuminating device according to (6), wherein
the light amounts of the emission light beams are changed on the basis of the correlation in a manner that each of the emission light beams has identical luminance.

(8)

The control method for an illuminating device according to (6), wherein
a luminance ratio of each of the emission light beams is changed on the basis of the correlation while a light amount of illumination light obtained by multiplexing the emission light beams is maintained.

(9)

The control method for an illuminating device according to (6), wherein
a light amount of illumination light obtained by multiplexing the emission light beams is changed on the basis of the correlation while a luminance ratio of each of the emission light beams is maintained.

(10)

An image acquisition system including:
a plurality of light sources;
a light monitor unit configured to detect each of light amounts of emission light beams emitted from the light sources;
a light receiving unit configured to receive the emission light beams; and
a control unit configured to control each of the light amounts of the emission light beams on the basis of a correlation between luminance detected by the light receiving unit and the light amounts of the emission light beams.

(11)

The image acquisition system according to (10), including:
a calculation unit configured to calculate a correlation between each of the light amounts of the emission light beams and the luminance.

(12)

The image acquisition system according to (10) or (11), wherein
the image acquisition system is an endoscopic system or a microscopic camera device.

REFERENCE SIGNS LIST 10, 20 image acquisition system
100 illuminating device
110R red light source control unit
110G green light source control unit
110B blue light source control unit
130R red light source
130G green light source
130B blue light source
131 excitation light source
133, 135 condensing lens
137 optical crystal
139 resonator mirror
141 wavelength conversion element
143 reflection unit
150R red light monitor unit
150G green light monitor unit
150B blue light monitor unit
151R, 151G, 151B light sampler
153 mirror
155, 157 dichroic mirror
159 lens
170 multiplexing unit
180 multiplexing module
200 imaging processing device
210 optical system
230 light receiving unit
250 imaging processing unit
300 illuminating device
310R red light source drive control circuit
310G green light source drive control circuit
310B blue light source drive control circuit
330 control unit

The invention claimed is:

1. An illuminating device comprising:
a plurality of light sources including a red light source, a green light source, and a blue light source; and
circuitry configured to:
drive each of the plurality of light sources at each of a plurality of drive levels;
obtain light monitor values and luminance values for the red light source, the green light source, and the blue light source at each of the plurality of drive levels,
determine a calibration formula for each of the red light source, the green light source, and the blue light source based on correlations between the obtained light monitor values and the luminance values at each of the plurality of drive levels such that each light monitor value is associated with a respective luminance value, and
perform a white balance adjustment process that includes the circuitry being configured to (i) determine white balance target values for the red light source, the green light source, and the blue light source in accordance with the determined calibration formulas, and (ii) adjust a white balance of the illuminating device until the light monitor values coincide with the determined white balance target values for the red light source, the green light source, and the blue light source, respectively,
wherein, when the light monitor values coincide with the determined white balance target values, the red light source, green light source, and the blue light source produce the same luminance values.

2. The illuminating device according to claim 1, wherein the plurality of light sources are laser light sources.

3. The illuminating device according to claim 1, wherein the circuitry is further configured to
determine deteriorations in the light sources based on the light monitor values detected by a light monitor.

4. A control method for an illuminating device, the control method comprising:
driving each of a plurality of light sources including a red light source, a green light source, and a blue light source at each of a plurality of drive levels;
detecting each of light amounts of emission light beams emitted from the plurality of light sources at each of the plurality of drive values;
obtaining light monitor values and luminance values at each of the plurality of drive values for the red light source, the green light source, and the blue light source;
determining a calibration formula for each of the red light source, the green light source, and the blue light source based on correlations between the obtained light monitor values and the luminance values at each of the plurality of drive levels such that each light monitor value is associated with a respective luminance value, and performing a white balance adjustment process that includes (i) determining white balance target values for the red light source, the green light source, and the blue light source in accordance with the determined calibration formulas, and (ii) adjusting a white balance of the illuminating device until the light monitor values coincide with the determined white balance target values for the red light source, the green light source, and the blue light source, respectively, wherein, when the light monitor values coincide with the determined white balance target values, the red light source, green light source, and the blue light source produce the same luminance values.

5. The control method for the illuminating device according to claim 4, wherein the luminance ratio of each of the emission light beams is changed based on calibration formulas while the constant light amount of illumination light obtained by multiplexing the emission light beams is maintained.

6. The control method for the illuminating device according to claim 4, wherein the constant light amount of illumination light obtained by multiplexing the emission light beams is changed based on the calibration formulas while the luminance ratio of each of the emission light beams is maintained.

7. An image acquisition system comprising:
a plurality of light sources including a red light source, a green light source, and a blue light source;
an image processing device configured to
receive emission light beams; and
circuitry configured to
drive each of the plurality of light sources at each of a plurality of drive levels;
detect the emission light beams emitted from the plurality of light sources,
obtain light monitor values and luminance values for the red light source, the green light source, and the blue light source at each of the plurality of drive levels,
determine a calibration formula for each of the red light source, the green light source, and the blue light source based on correlations between the obtained light monitor values and the luminance values at each of the plurality of drive levels such that each light monitor value is associated with a respective luminance value, and
perform a white balance adjustment process that includes the circuitry being configured to (i) determine white balance target values for the red light source, the green light source, and the blue light source in accordance with the determined calibration formulas, and (ii) adjust a white balance of the illuminating device until the light monitor values coincide with the determined white balance target values for the red light source, the green light source, and the blue light source, respectively,
wherein, when the light monitor values coincide with the determined white balance target values, the red light source, green light source, and the blue light source produce the same luminance values.

8. The image acquisition system according to claim 7, wherein the image acquisition system is an endoscopic system or a microscopic camera device.

9. The illuminating device according to claim 1, wherein the circuitry is further configured to perform a color temperature adjustment process that includes the circuitry being configured to (i) determine color temperature target values for the red light source, the green light source, and the blue light source in accordance with the determined calibration formulas, and (ii) adjust a color temperature of an illumination light of the illumination device by changing a luminance ratio of red, green, and blue lights included in the illumination light while maintaining a constant light amount of the illumination light until the light monitor values coincide with the determined color temperature target values for the red light source, the green light source, and the blue light source, respectively.

10. The illuminating device according to claim 9, wherein the circuitry configured to determine color temperature target values is further configured to:
calculate a total luminance value corresponding to the light monitor values based on the determined calibration formulas;
calculate luminance values for the red, green, and blue lights based on the luminance ratio, wherein the sum of the calculated luminance values equals the total luminance; and
calculate the color temperature target values according to the calculated luminance values based on the determined calibration formulas.

11. The control method for the illuminating device according to claim 4, further comprising:
performing a color temperature adjustment process that includes (i) determining color temperature target values for the red light source, the green light source, and the blue light source in accordance with the determined calibration formulas, and (ii) adjusting a color temperature of an illumination light of the illumination device by changing a luminance ratio of red, green, and blue lights included in the illumination light while maintaining a constant light amount of the illumination light until the light monitor values coincide with the determined color temperature target values for the red light source, the green light source, and the blue light source, respectively.

12. The control method for the illuminating device according to claim 11, wherein determining the color temperature target values further comprises:
calculating a total luminance value corresponding to the light monitor values based on the determined calibration formulas;
calculating luminance values for the red, green, and blue lights based on the luminance ratio, wherein the sum of the calculated luminance values equals the total luminance; and
calculating the color temperature target values according to the calculated luminance values based on the determined calibration formulas.

13. The image acquisition system according to claim 7, wherein the circuitry is further configured to perform a color temperature adjustment process that includes the circuitry being configured to (i) determine color temperature target values for the red light source, the green light source, and the blue light source in accordance with the determined calibration formulas, and (ii) adjust a color temperature of an illumination light of the illumination device by changing a luminance ratio of red, green, and blue lights included in the illumination light while maintaining a constant light amount of the illumination light until the light monitor values coincide with the determined color temperature target values for the red light source, the green light source, and the blue light source, respectively.

14. The image acquisition system according to claim 13, wherein the circuitry configured to determine color temperature target values is further configured to:
- calculate a total luminance value corresponding to the light monitor values based on the determined calibration formulas;
- calculate luminance values for the red, green, and blue lights based on the luminance ratio, wherein the sum of the calculated luminance values equals the total luminance; and
- calculate the color temperature target values according to the calculated luminance values based on the determined calibration formulas.

\* \* \* \* \*